(12) United States Patent
Hugg et al.

(10) Patent No.: US 10,502,844 B2
(45) Date of Patent: Dec. 10, 2019

(54) SPARSE ACQUISITION GAMMA CAMERAS

(71) Applicant: Kromek Group, PLC, County Durham (GB)

(72) Inventors: James W. Hugg, Mars, PA (US); Brian W. Harris, Gibsonia, PA (US)

(73) Assignee: KROMEK GROUP, PLC, County Durham (GB)

( * ) Notice: Subject to any disclaimer, the term of this patent is extended or adjusted under 35 U.S.C. 154(b) by 0 days.

(21) Appl. No.: 15/473,336

(22) Filed: Mar. 29, 2017

(65) Prior Publication Data

US 2017/0285191 A1    Oct. 5, 2017

Related U.S. Application Data

(60) Provisional application No. 62/314,453, filed on Mar. 29, 2016.

(51) Int. Cl.
*G01T 1/24* (2006.01)
*A61B 6/03* (2006.01)
*A61B 6/00* (2006.01)

(52) U.S. Cl.
CPC .......... *G01T 1/249* (2013.01); *A61B 6/037* (2013.01); *G01T 1/243* (2013.01); *A61B 6/4275* (2013.01); *A61B 6/483* (2013.01)

(58) Field of Classification Search
CPC ........ G01T 1/249; G01T 1/2002; A61B 6/037
See application file for complete search history.

(56) References Cited

U.S. PATENT DOCUMENTS

2013/0320222 A1* 12/2013 Abenaim ............... A61B 6/032
                                                           250/366
2017/0192107 A1*  7/2017 Li ......................... G01T 1/1603

OTHER PUBLICATIONS

"A compact, discrete CsI(Tl) scintillator/Si photodiode gamma camera for breast cancer imaging," Lawrence Berkeley National Laboratory, LBNL Paper LBNL-47620, published Dec. 1, 2000 to Gruber.*

* cited by examiner

*Primary Examiner* — Kenneth J Malkowski
(74) *Attorney, Agent, or Firm* — Ference & Associates LLC (57) ABSTRACT

An imaging method and device are described for improving the performance of a gamma camera by optimizing a figure of merit that depends upon cost, efficiency, and spatial resolution. In a modular gamma camera comprising a tiled array of gamma detector modules, the performance figure of merit can be optimized by sparsely placing gamma detector modules within the gamma camera, optimizing collimation, and providing means for detector and/or collimator motion. Sparse gamma cameras can be constructed as flat or curved panels, and elliptical or circular rings.

28 Claims, 8 Drawing Sheets

SPARSE ACQUISITION GAMMA CAMERAS

CROSS-REFERENCE TO RELATED APPLICATION

This application claims priority from and benefit of U.S. Provisional Patent Application No. 62/314,453 filed on Mar. 29, 2016 and titled "Sparse Acquisition CZT Gamma Cameras," the subject matter of which is hereby incorporated by reference in its entirety

FIELD OF THE INVENTION

The principal application addressed by this invention is Gamma Cameras, in general, and specifically Single-Photon Emission Computed Tomography (SPECT). The principle field of application is Nuclear Medicine (also known as "Molecular Imaging") which images gamma photon emission (SPECT) following injection of a radioisotope labelled tracer (molecular imaging agent) into a patient's vein. The tracer is taken up by certain target tissues and the attached radioisotope continuously decays. The emitted gamma photons are imaged by a gamma camera, or preferably, two or more gamma cameras. In the case of single-photon emission (as in SPECT), a collimator (e.g., parallel or focused hole, slit-slat, rotating slat, multiple pinhole, or coded aperture) is integral to the effective functioning of the gamma camera. It is also possible to use a Compton scatterer (also known as "electronic collimation"), either within the gamma camera or in a separate device such as one or more Si position sensitive detectors, to detect Compton scattered events in the gamma camera and to form images by 3D reconstruction. In other related applications of gamma cameras, such as security screening detection of contraband radioactive sources or astronomical mapping of x-ray or gamma photon sources, coded aperture collimation may be employed. Gamma cameras can be employed in baggage scanning using, for example, coded aperture x-ray scatter (diffraction) imaging. The examples are only illustrative; this invention applies to all applications of gamma cameras.

This invention provides practical designs especially for semiconductor solid-state direct conversion detector based gamma or x-ray cameras, such as those using Cadmium-Zinc-Telluride (CdZnTe or CZT), Cadmium-Telluride (CdTe), or Mercuric Iodide (HgI). Some embodiments of the invention are based upon the concept of using fewer detector elements than a fully populated detector array would use, so these embodiments are labeled as "sparse acquisition." Other embodiments apply other concepts, so the sparse acquisition label should not be considered a limiting element of this invention.

BACKGROUND OF THE INVENTION

Gamma cameras, also known as scintillation cameras or Anger cameras, have been used for over half a century to image gamma photon emission in a technique known as scintigraphy. They are applied in nuclear medicine imaging (also known as "molecular imaging") to view images of the interior tissues of the human body containing a distribution of medically injected, inhaled, or ingested radiopharmaceuticals emitting gamma photons. They can also be used in security screening or astronomical imaging applications to detect and image gamma photons arising from radioactive sources or astrophysical sources of x-rays and/or gamma photons. Hal Anger developed the first gamma camera in 1957 and variations on his design are still widely used today.

A typical gamma camera comprises a large planar crystal (about 40 cm×54 cm×0.95 cm) of sodium iodide with thallium doping, labelled NaI(Tl), in a hermetically sealed container that prevents moisture and visible light from reaching the crystal. The back face has a transparent glass window or light guide. The crystal scintillates when a gamma photon strikes it and the scintillation light can escape through the window, where an array of photodetectors (such as vacuum photomultiplier tube—PMT, or multichannel plate—MCP, or silicon photomultiplier—SiPM) are coupled through optical gel. The location of the gamma photon interactions in the NaI crystal are determined by a weighting of the current or voltage responses of multiple PMTs that detect the scintillation light.

A gamma camera is typically coupled with a collimator (for example: parallel or focused hole, slit-slat, rotating slat, multiple pinhole, or coded aperture) that acts as a lens for forming a projection image. In SPECT, used in nuclear medicine, a 3D image is formed by moving the gamma camera to multiple angular positions around the patient, acquiring planar projections at each position, and then reconstructing a 3D image of the gamma emission source distribution using various techniques, such as filtered back-projection or iterative maximum likelihood estimation reconstruction. OSEM, Ordered Subset Expectation Maximization, is the currently preferred method. Commercial SPECT systems most commonly consist of two gamma cameras mounted in opposition (180 degree angle) or side-by-side (forming a 90 to 120 degree angle) on a gantry with a patient table positioned between the slowly rotating gamma cameras.

This invention addresses one or more limitations of current commercial solutions and prior art. In particular, the basic technology used in gamma cameras has not changed substantially since 1957, except that computers have increased the efficiency of the data acquisition and image reconstruction. This invention concerns in part the introduction of solid-state semiconductor gamma detectors arrayed as a gamma camera. By way of illustration, pixelated Cadmium-Zinc-Telluride (CdZnTe or CZT) detectors will be referenced, although similar considerations apply to other solid-state gamma detectors, such as Cadmium-Telluride (CdTe) and Mercuric Iodide (HgI). These pixelated solid-state detectors have many advantages over the prior art consisting of a scintillator (such as sodium iodide (NaI), cesium iodide (CsI), lanthanum bromide (LaBr), etc.) and photodetector (such as photomultiplier tube (PMT), multi-channel plate (MCP), silicon photomultiplier (SiPM), avalanche photodiode (APD), etc.), but they also have the disadvantage of having a higher cost than the 60-year old prior art.

This invention also applies in part to non-pixelated detectors, such as crossed-strip or position-sensitive virtual Frisch grid designs. This invention addresses one or more ways to decrease the cost of solid-state gamma cameras, primarily by sparsely placing the CZT detector modules and then compensating with novel collimation and image reconstruction. Although we will discuss CZT gamma cameras, many of the same design principles could apply to small (less than about 400 cm² area, but preferably less than about 25 cm² area) modular scintillator cameras and such generalizations are intended by this invention.

Figure 1:
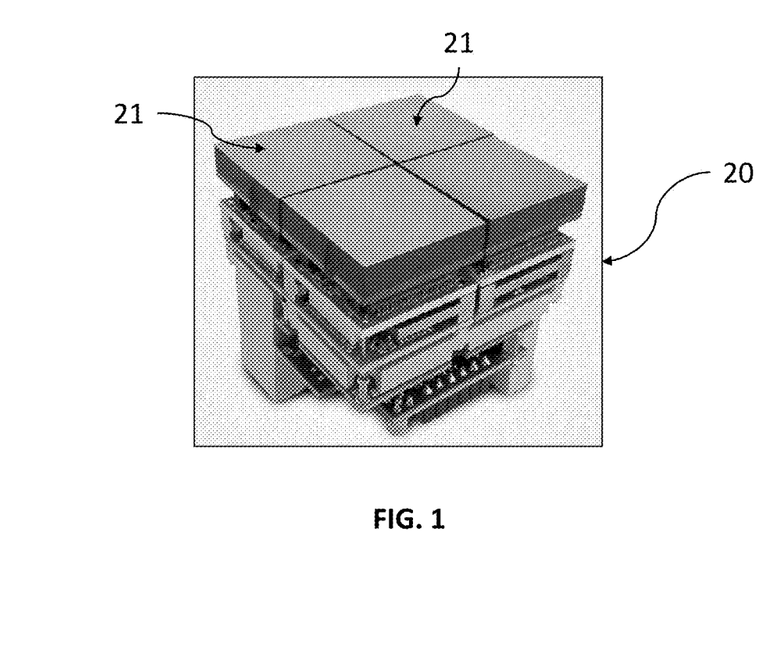
FIG. 1 is a pixelated CZT detector module of the preferred embodiment of the invention.

By way of example, we will discuss a preferred embodiment of a CZT gamma camera 22 consisting of an array of modular pixelated CZT detectors (called D-Matrix™) that we have designed and tested. The basic module is shown in FIG. 1 and consists of four CZT gamma modules (GM) 21 in a 2×2 array comprising one aggregator module (AM) 20. Each AM 20 is 4.4 cm square and provides digital signal output including 2D location (module and pixel numbers or, preferably, x and y) and energy for each gamma photon detection event. Optionally, a 3D location including depth of interaction z in the CZT crystal can also be provided. One skilled in the art will appreciate that the AM 20 includes ASICs (application-specific integrated circuits), one or more ADCs (analog to digital converters), and potentially an FPGA (field-programmable gate arrays) as well as supporting input/output electronics. Table 1 following contains the preferred characteristics of each CZT gamma detector aggregator module 20.

TABLE 1

Features of a D-Matrix™ CZT gamma detector aggregator module (AM), 20, as shown in FIG. 1.

| Feature | Specification |
| --- | --- |
| Aggregator Module (AM) detection area | 4.4 cm × 4.4 cm |
| Pixel pitch | 2 mm |
| CZT thickness | 0.5 cm (or optional 1.0 cm) |
| Footprint | Tileable on 4 sides |
| Energy range | 30 keV to 400 keV |
| Operating environmental temperature range | 20° C. to 35° C. |
| Data output (list mode) | x, y, energy, (optional: z [depth of interaction] and various event timings) |
| API | Software for acquisition computer interface |

Figure 2:
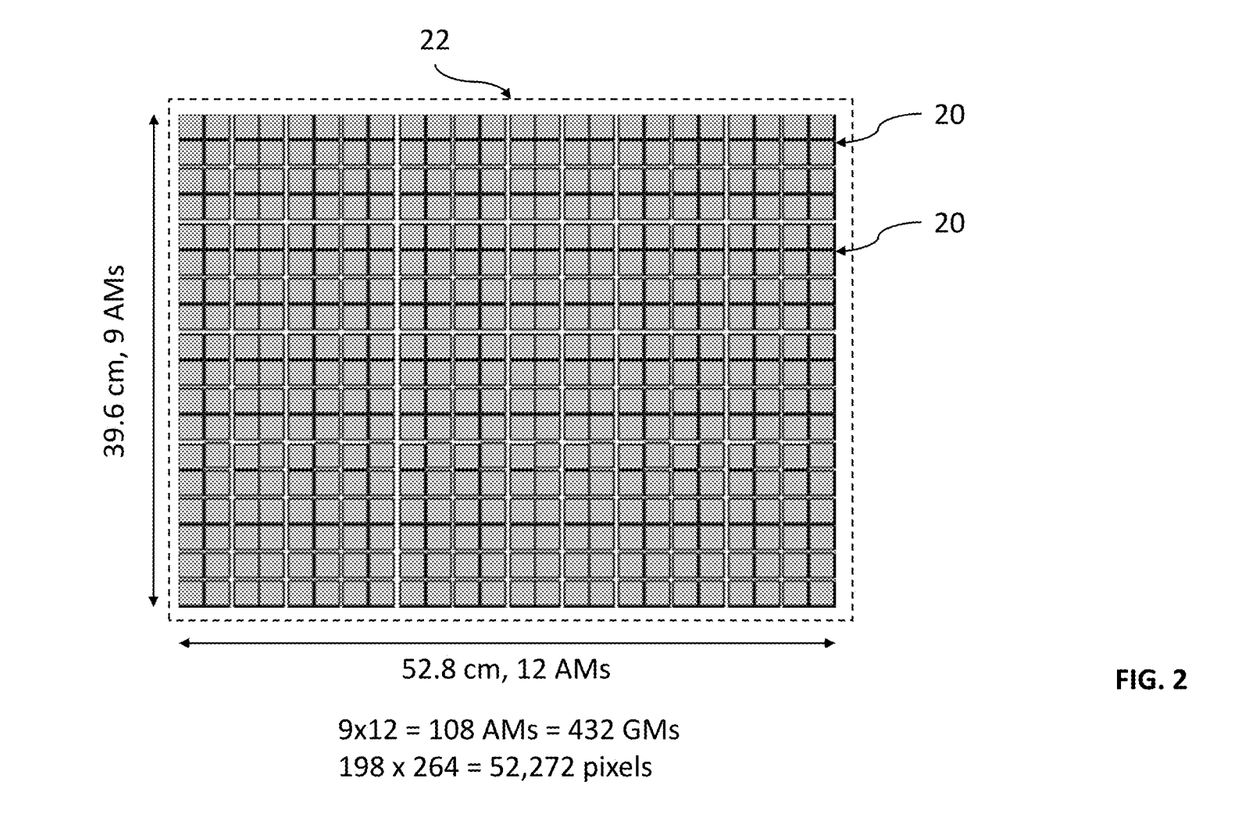
FIG. 2 is an illustration of an array of the CZT detector module of FIG. 1 in a size appropriate for a general purpose flat panel SPECT gamma camera.

By way of further example, we will discuss a gamma camera 22 composed of D-Matrix™ aggregator modules 20 arrayed in a size compatible with a general-purpose SPECT system as depicted in FIG. 2. In the illustration, nine AMs 20 are arrayed in each of 12 columns, each 39.6 cm long and 4.4 cm wide. The 12 adjacent columns comprise a camera 52.8 cm wide. Thus, there are a total of nine×12=108 AM 20, and 4×108=432 GM 21. Since each GM 21 has 121 pixels, the general purpose gamma camera 22 in FIG. 2 has 52,272 pixels, each two mm square. Some of the advantages of a CZT gamma camera compared to a scintillator gamma camera can be seen in Table 2 following.

TABLE 2

Comparison of typical scintillator gamma camera to a CZT gamma camera composed of an array of D-Matrix™ CZT detector aggregator modules.

| Compared Metric | NaI & PMTs cameras | modular CZT cameras |
| --- | --- | --- |
| Detector Crystal Thickness | 0.95 cm thick NaI(Tl) | 0.5 cm thick CZT or 1.0 cm thick CZT (option) |
| Camera Useful Field of View | 40.6 cm × 54 cm | 39.6 cm × 52.8 cm (no dead edges) |
| Intrinsic Spatial Resolution | 3.3 mm FWHM Gaussian | 2.0 mm square pixels |
| Intrinsic Pixels per Camera (Space-Bandwidth Product) | 20,132 with Gaussian overlap | 52,272 square, no overlap |
| Intrinsic Energy Resolution | ≤9.6% FWHM @ 140 keV | ≤4.0% FWHM @ 140 keV |

Table 2 shows that CZT detectors can be arrayed in a camera size similar to a typical commercial gamma camera (most are about 40 cm axial×54 cm transaxial). The five mm thickness of CZT is chosen to provide a similar stopping power to a typical 0.95 cm (⅜″) thick NaI scintillator. This thickness is adequate for the most common medical isotopes, such as Tc-99m (140 keV), Tl-201 (70 keV), Xe-133 (81 keV), Ga-67 (90 keV), and I-123 (159 keV). Increasing the CZT thickness to 1.0 cm will increase the stopping power and thus the detection efficiency for higher energy medical isotopes, such as In-111 (171 & 245 keV) and I-131 (364 keV), although at considerable increase in cost.

The intrinsic spatial resolution of the example CZT gamma camera 22 is about 1.7 times better than a typical scintillator gamma camera 22 resulting in 2.7 times more pixels in the same detector area. Moreover, the pixelated CZT gamma camera has no dead edges compared to the scintillation camera which has unusable ("dead") edges about half the diameter of the PMTs wherein the Anger position determination is ineffective. Thus the edges of a scintillation camera must typically be masked off and not used for imaging. Furthermore, a scintillation gamma camera has a nonuniform performance wherein the central field of view CFOV performs significantly better than the peripheral ("useful") field of view UFOV. In a CZT gamma camera the performance is uniform across the full surface, so the CFOV and UFOV performance is equal. Furthermore, the CZT pixels are square and non-overlapping (except for a small amount of charge sharing), while the scintillator pixels are Gaussian with considerable overlap between neighboring pixels. Finally, the energy resolution is typically 2.4 or more times better, resulting in a better discrimination against scattered gamma photons which blur SPECT images.

We tabulated the price that our customers paid for CZT gamma detectors mounted on substrates with connectors for attachment to ASICs and other read-out electronics and determined the price per area ($/cm$^2$) of CZT gamma detectors since 2000. The price of CZT gamma cameras has been driven down exponentially (with a half-life of about 4 years) by improvements in CZT crystal growth and sensor fabrication. The relative prices are now only two to four times greater for CZT gamma cameras compared to NaI & PMTs. The purpose of this invention disclosure is to provide additional system design steps that can offer an additional factor of two or more reduction in the cost of CZT gamma cameras, principally by sparsely populating the cameras with CZT detectors, then compensating with collimator design and optional detector and/or collimator motion to achieve similar examination times for the improved image quality that CZT gamma cameras offer.

BRIEF SUMMARY OF THE INVENTION

This invention provides an imaging method and device for improving the performance of a gamma camera by optimizing a figure of merit that depends upon cost, efficiency, and resolution. In a modular gamma camera comprising a tiled array of gamma detector modules, the performance figure of merit can be optimized by sparsely placing gamma detector modules within the gamma camera, optimizing collimation, and providing means for detector and/or collimator motion. The method includes predetermining the performance requirements for specific applications, choosing a gamma camera architecture (such as flat or curved panel, or elliptical or circular ring), choosing a collimation scheme (such as parallel or focused hole, slit-slat, rotating slat, multi-pinhole, coded aperture, or Compton scatter), then optimizing the figure of merit through simulations. The simulation steps include simulating a source distribution of radioactive material, modeling the physics of the system and acquisition sequence, iteratively reconstructing the model data, and calculating a figure of merit for that particular configuration. The optimization steps require sparsely placing gamma detector modules (or equivalently, removing modules from a fully populated design), optimizing collimation, and potentially providing a means for detector and/or collimator motion.

In one embodiment of the invention, the sparse placement of more expensive semiconductor (such as CZT) gamma detectors is accomplished by employing one scintillator gamma camera and one semiconductor gamma camera contemporaneously in the same SPECT imaging system. This solution reduces cost considerably, compared to a dual semiconductor gamma camera system, while providing reconstructed images with much of the benefit of the semiconductor gamma camera.

Another embodiment of this invention provides for removal of alternating columns or rows of semiconductor gamma detectors, so that only 50% of the gamma camera area is occupied. It is beneficial to provide movement for these slat detectors so that they spend about half of the time in one position and half in the position of the removed detectors.

Another embodiment of this invention provides for removal of blocks of gamma detector modules in a checkerboard pattern. We disclose that multi-pinhole collimation is particularly beneficial when the detector blocks are large enough to enable overlapping pinhole projections that can be reconstructed faithfully for quite large degrees of overlap.

Another embodiment of this invention provides for circular or elliptical rings of tiled gamma detector modules. These rings can be sparsely populated and the multi-pinhole, focused hole, or slit-slat collimation can be optimized in the same manner as described for flat or curved panel gamma cameras. The figure of merit can be quite high for such systems and this is the preferred embodiment of the invention. However, detector ring SPECT is likely not the first commercial step, as evidenced by the introduction of a flat panel CZT SPECT system by GE Healthcare.

BRIEF DESCRIPTION OF THE DRAWINGS

The organization and manner of the structure and operation of the invention, together with further objects and advantages thereof, may best be understood by reference to the following description, taken in connection with the accompanying non-scale drawings, wherein like reference numerals identify like elements in which.

DETAILED DESCRIPTION OF THE ILLUSTRATED EMBODIMENTS

While the invention may be subject to embodiment in different forms, there are shown in the drawings, and herein will be described in detail, specific embodiments with the understanding that the present invention is to be considered an exemplification of the principles of the invention, and is not intended to limit the invention to that as illustrated and described herein.

FIG. 1 shows a modular solid-state direct conversion CZT gamma detector called D-Matrix™. This aggregator module (AM) 20 is composed of four CZT crystal detectors 21, each designated a gamma module (GM), each measuring about 2.2 cm×2.2 cm×0.5 cm thick. Each GM 21 may comprise a monolithic crystal or may comprise multiple tiles of CZT mounted in an abutting composite with small gaps between the tiles. The top GM 21 surface in FIG. 1 is the metallic cathode, which is typically monolithic but which can also be pixelated. Gamma photons generally enter the GM from the cathode side of the CZT crystal. The lower surface of the GMs 21 has metallic anode pixels with a pitch of about two mm in an 11×11 pixel pattern for each CZT detector. The CZT is bonded to a substrate that provides mechanical stability and electrical connections to the read-out electronics boards, which include ASICs, one or more ADCs, and an FPGA. Negative DC bias voltage (about −500 V for 0.5 cm thick CZT) is provided for the cathodes and an optional capacitive decoupling circuit allows reading the induced cathode signal as well as the anode signals. The overall dimension of the D-Matrix™ aggregator module (AM) 20 with 4 GMs 21 (CZT detectors, 0.5 cm thick) and readout electronics is about 4.4 cm×4.4 cm×5 cm thick. This AM 20 can be tiled to comprise various sized arrays to constitute flat panels, curved panels, rings, ellipses, or other structures as will be disclosed in this invention. Some of the features of the AM 20 are listed in Table 1.

One of the advantages of CZT gamma detectors is that they occupy a smaller volume than scintillators and PMTs, so that CZT gamma cameras can be shielded by less volume and weight of heavy metal, such as lead (Pb) or tungsten (W). Thus a SPECT system gantry designed specifically for a CZT gamma camera can be smaller and lighter than a conventional SPECT gantry. It may have a smaller footprint and fit into a smaller examination room.

Furthermore, the energy resolution of a CZT gamma camera, as listed in Table 2, is much better (about 4% or less compared to about 9.6% for NaI). Practically, this means that a narrower energy window can be used for the photopeak projection images that are reconstructed into 3D SPECT images. This narrower energy window will discriminate against scattered gamma photons which blur the SPECT image. Thus, the final image contrast should significantly improve in a CZT camera compared to a scintillation gamma camera.

FIG. 2 depicts one such array 22 of AMs 20 (only two of 108 are labelled) in a size typical of flat panel gamma cameras used in general purpose medical SPECT. The illustrative array 22 comprises nine rows and 12 columns of AMs 20 forming a flat panel gamma camera 22 with dimensions of about 39.6 cm×52.8 cm. This illustrative arrangement comprises nine×12=108 AMs and (nine×22)×(12×22)=198×264=52,272 pixels, as tabulated in Table 2.

The original gamma camera built by Hal Anger in 1957 was a flat panel detector with a circular field of view. All commercial clinical gamma cameras have been derivatives of the original flat panel, although the field of view became rectangular in the 1980s when 3D tomographic image reconstruction from SPECT became practical. There have been several attempts to use curved scintillation cameras for brain or heart imaging applications, but none have been commercially successful. Several small-animal preclinical SPECT systems were built using CZT modules in a ring, but these have not been sold in any successful quantities. Nevertheless, modular detector assemblies, such as the Aggregator Module, AM 20, of FIGS. 1 and 2 are amenable to forming a curved arcuate surface, or ring, or ellipse of detectors.

Figure 3:
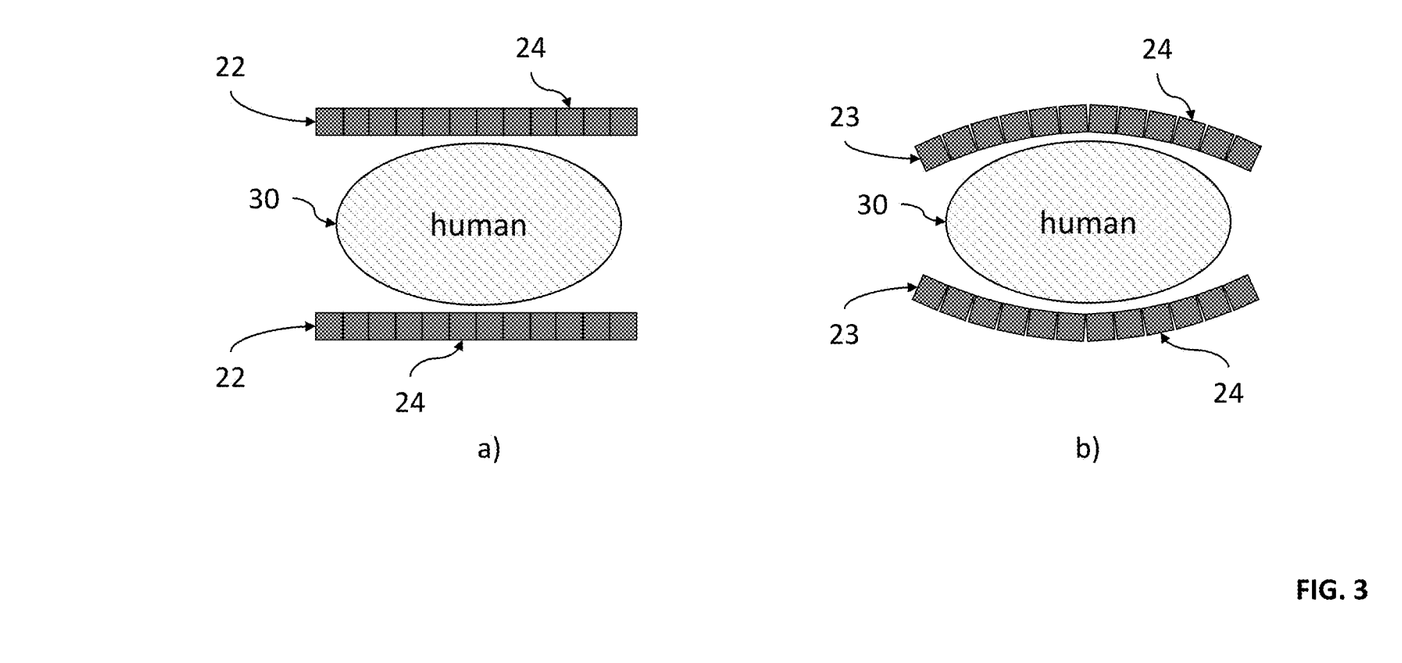
FIG. 3 illustrates a transaxial view of a human body surrounded by two opposed SPECT scanning CZT gamma cameras in either a flat panel or concave curved panel configuration.

FIGS. 3(a) and 3(b) illustrate this design option for a curved detector surface. FIG. 3(a) illustrates a transaxial cross-section (view from the patient's feet) of a dual-detector SPECT system with a human body 30 as the example object being imaged by gamma emission. Both detector arrays 22 in FIG. 3a, as in FIG. 2, are shown in cross-section with 12 columns 24 illustrated by gray boxes. By reference to FIG. 2, it is apparent that each column 24 comprises nine AMs 20 with length about 39.6 cm. Not shown explicitly are collimators, radiation shielding, and readout electronics, but these elements are well known by those of skill in the art. FIG. 3(b) illustrates curved arcuate surface detectors 23 that could be formed by placing the columns 24 of AMs 20 along a curved surface that roughly follows the contour of a typical human body.

A gamma camera could be designed to mechanically transform between the flat panel configuration of FIG. 3(a) and the curved panel configuration of FIG. 3(b). It is anticipated that the curvature could be fixed or variable. The reconstruction would be easier for a fixed curvature, but if the position of each detector is tracked mechanically or by other means, then the iterative reconstruction software could accommodate "body contouring" with variable curve panels. As will be apparent to those skilled in the art, the hinge points for such a transformation would depend upon the collimation scheme employed. For example, if parallel hole collimators were attached to each CZT detector column 24, then the hinge-points would be at the front face of the collimator columns. However, if multiple-pinhole collimation were employed, the hinge points would be at the front face of the CZT detectors 21 of FIG. 1.

The smaller square pixels of a CZT gamma camera can also be used to advantage compared to the larger overlapping Gaussian pixels of a scintillation gamma camera. Collimators can be designed (not the subject of the present invention) to optimize the spatial resolution and efficiency of the detector-collimator system, again improving the image contrast. By way of illustration, Table 3 shows a comparison of typical hexagonal parallel-hole collimators, as used in most clinical SPECT systems, and some possible pixel-registered square-hole collimators. These design concepts have not been optimized, but are illustrative of the performance achievable with such pixelated CZT specific collimators.

TABLE 3

Comparison of typical SPECT collimators and potential CZT-specific collimators.

| Type parallel hole Pb | Hole Shape | Size (mm) | Septa (mm) | Length (mm) | Penetration @ 140 keV | Efficiency (cpm/μCi) | Resolution (mm) @ 0 cm | Resolution (mm) @ 10 cm | Resolution (mm) @ 20 cm |
|---|---|---|---|---|---|---|---|---|---|
| typical LEGP | Hexagonal | 1.40 | 0.18 | 24.7 | 2.1% | 277 | 3.9 | 8.9 | 14.7 |
| typical LEHR | Hexagonal | 1.22 | 0.15 | 27.0 | 1.7% | 168 | 3.7 | 7.4 | 11.9 |
| LEGP-CZT | Square | 1.80 | 0.20 | 31.0 | 1.6% | 356 (+29%) | 2.2 | 8.9 | 15.6 |
| LEHR-CZT | Square | 1.85 | 0.15 | 40.9 | 1.8% | 226 (+35%) | 2.2 | 7.4 | 12.6 |

Figure 4:
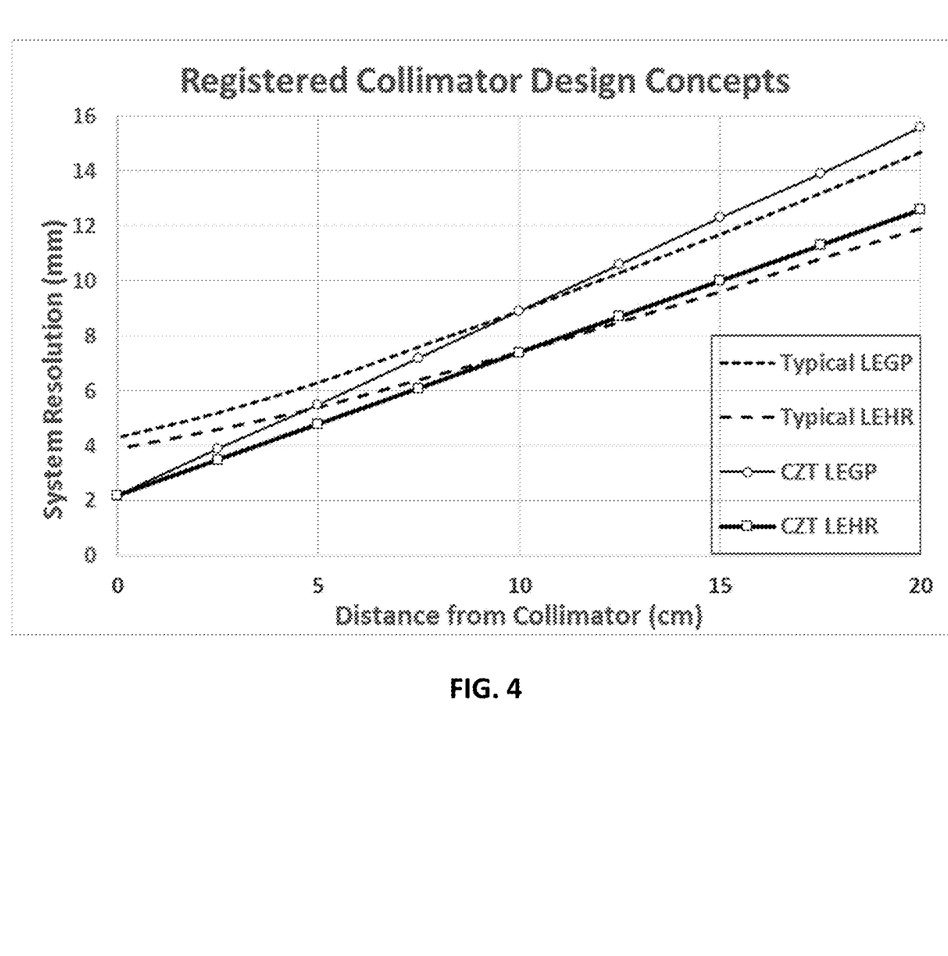
FIG. 4 is a graph comparing the planar system resolution for scintillator and CZT gamma cameras using registered square-hole collimator concepts.

FIG. 4 shows graphically the comparison of the four collimators shown in Table 3. The dashed curves represent the system resolution for typical LEGP (Low Energy General Purpose, short dash) and LEHR (Low Energy High Resolution, longer dash) hexagonal parallel-hole lead (Pb) collimators. By way of illustration, the solid lines represent the system resolution for two potential designs for pixel-registered square-parallel-hole lead (Pb) collimators. The thinner solid line with open circle markers represents the LEGP-CZT collimator response; the thicker solid line with open square markers represents the LEHR-CZT collimator response. The system resolution at 10 cm distance from the face of the collimator was matched for the two LEGP and two LEHR collimators, as an example of a possible design. Of course the resolution as a function of distance from the collimator can be traded off for system efficiency (sensitivity). For the particular choice illustrated in FIG. 4 and TAB. 3, the registered LEGP-CZT is 29% more efficient than the typical clinical hexagonal hole LEGP collimator. Likewise, the LEHR-CZT is 35% more efficient than the typical clinical hexagonal hole LEHR collimator. The optimization of the design depends on the application task and could be accomplished by Monte Carlo modeling simulation of the system response coupled with iterative reconstruction employing a full physics description of the detector-collimator response.

As will be apparent to one skilled in the art, a pixel-registered collimator response has no significant dependence on the detector spatial resolution, hence the system resolution response function is approximately a straight line. In contrast, for a scintillator with Gaussian pixels, the system resolution is a quadrature summation of the detector and collimator resolutions, hence the resolution response function is approximately parabolic. The advantage for closer distances belongs to the CZT gamma camera with pixel-registered collimator. It will be apparent to one skilled in the art that the spatial resolution for a square-hole collimator is not isotropic in the plane. In our experience with such collimators as used in Molecular Breast Imaging (MBI), this off-axis resolution is not a significant issue.

Figure 5:
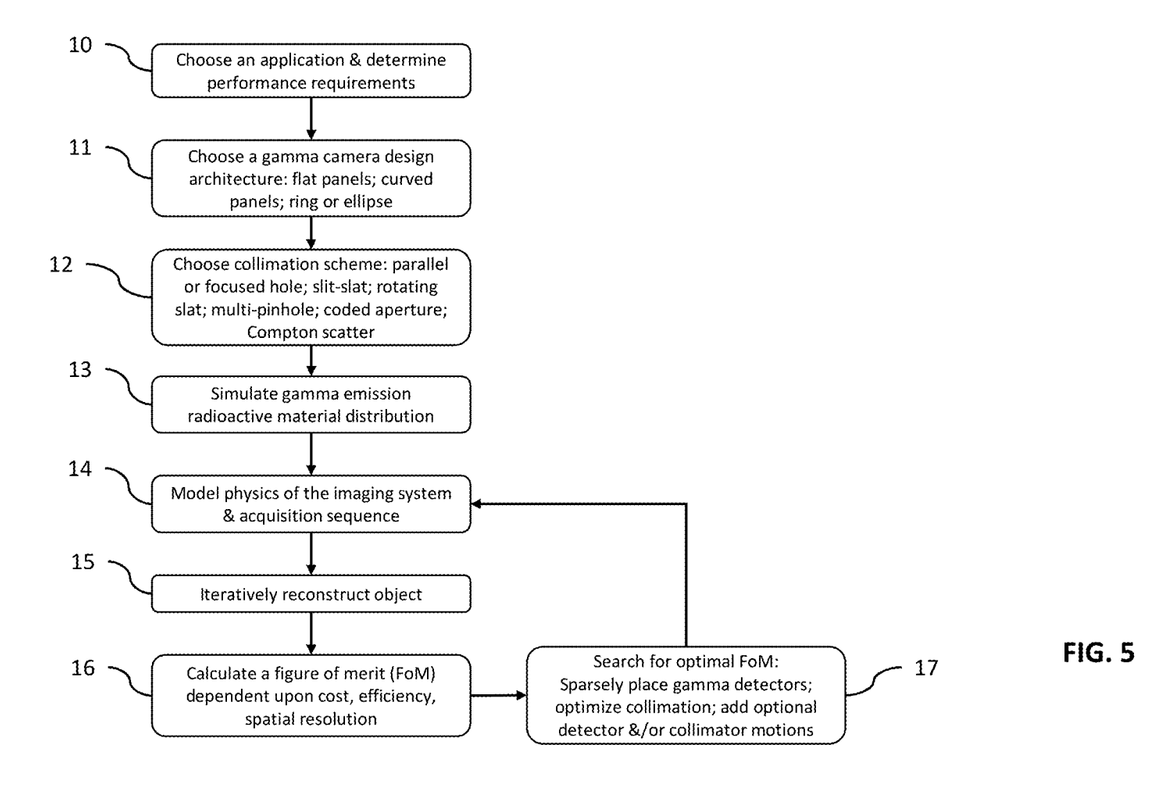
FIG. 5 is a process flow diagram depicting optimization of a performance figure of merit for a gamma camera based on sparely placed gamma camera modules.

FIG. 5 depicts a process flow diagram that can be followed to improve or optimize the design and operation of a CZT gamma camera. We first describe a simple Figure of Merit (FoM) that illustrates one way to optimize the gamma camera by seeking configurations that maximize the FoM. By way of illustration, we choose a simple function that represents performance and cost. A common rule of thumb for gamma camera performance is the ratio of Efficiency (often called sensitivity) and the square of system resolution. We further want to consider cost and make a simplifying assumption that performance and cost are equally weighted. Thus, one possible FoM=Efficiency/(Cost*Resolution$^2$). The step of calculating this FoM for any particular SPECT system is shown as step 16 in FIG. 5 and the goal (step 17) is to search for an optimal (maximum, in this case) FoM.

As shown in FIG. 5, the first step 10 in this optimization process is to choose an application and determine performance requirements. This introduces constraints on the design optimization. The next step 11 is to choose a gamma camera design architecture. In current SPECT systems the gamma cameras are flat panels. As FIG. 3 reminds us, CZT detectors can be configured as curved panels. As we will discuss in FIG. 8, circular or elliptical detector surfaces can also be formed with CZT detectors. The next step 12 is to choose a collimation scheme, which may comprise, for example, parallel or focused holes (hexagonal or registered square), slit-slat or rotating slat, multi-pinhole, coded aperture, or Compton (electronic collimation). The next step 13 is to simulate digitally an application object, typically a portion of a human body or a digital phantom with points, lines, and volumes of radioactivity. Excellent computational human phantoms exist for this purpose. Those skilled in the art will understand that step 13 can be performed before step 11 and/or step 12 without changing the results.

The next set of steps 14 through 17 are performed one or more times in an optimization loop. Step 14 considers the choices made in steps 11 and 12 for gamma camera geometry and collimation scheme. This imaging system and an acquisition sequence (for example, helical or stop-and-shoot SPECT) are modeled. Those skilled in the art understand that better results will generally be obtained when more of the physics of gamma emission imaging (such as collimator-detector response) are included in the model. For a particular distribution of radiopharmaceutical tracers in a computational phantom (step 13) the application of the forward projection model (step 14) will produce a simulation of the data that a physical system would acquire. This data set is usually called a sinogram for typical SPECT data acquisition. Step 15 applies iterative reconstruction algorithms, such as OSEM, to the sinogram data to produce a model of the object (step 13). The FoM is calculated in step 16. Typically, the efficiency and resolution can be assessed by using geometric objects as the computational phantom (step 13).

The first passage through the optimization loop (steps 14 through 17) establishes a baseline FoM. The next step 17 is to search for an optimal FoM by changing the imaging system and/or the imaging sequence. According to various embodiments of this invention to be discussed below, this optimization may be achieved by sparsely placing CZT gamma detectors 20 in a gamma camera, such as 22 or 23, and optionally adding detector and/or collimator motion to compensate for the "missing" detectors in the sparse arrangement. Steps 14 through 17 may be applied once or iteratively. The optimization process may be driven manually or by computer algorithms that assist the decisions about which gamma detectors 20 to eliminate in a sparse design. Below we will present several embodiments of this invention and will estimate the FoM for each configuration. To be performed rigorously, all the optimization process steps 10 through 17 should be performed. However, to illustrate the invention, steps 13 and 15 have not been performed and steps 14 and 16 have been approximated with simple models.

Flat Panel CZT Gamma Cameras

Figure 6:
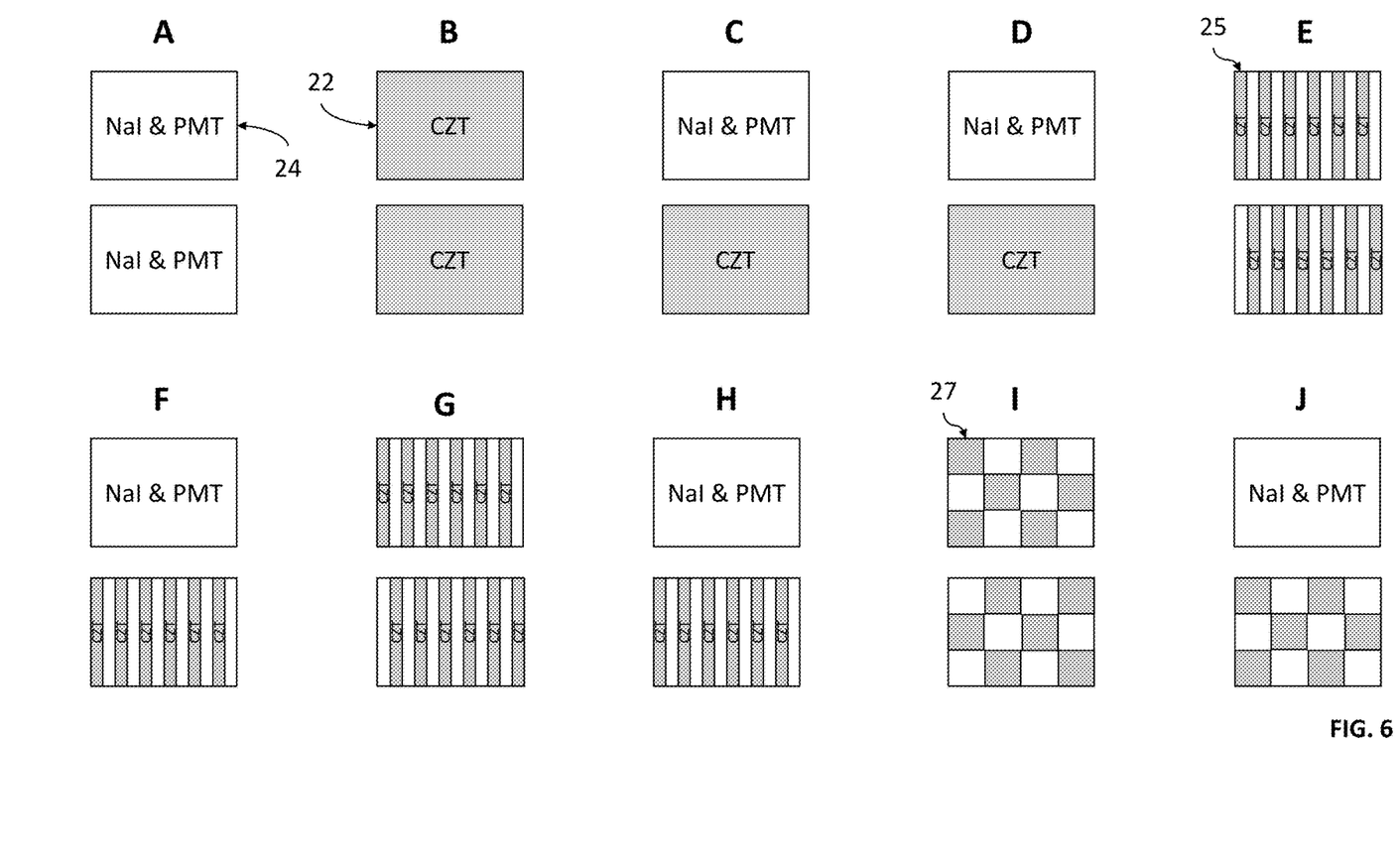
FIG. 6 depicts multiple possible configurations of flat panel CZT gamma cameras in which sparse placement of detector modules is achieved in various ways.

FIG. 6 depicts pairs of gamma cameras labeled A through J. Each pair is shown side by side in a view from the patient. In clinical practice, the pair of gamma cameras would be mounted in opposition (or at about a right angle) on a SPECT gantry. The pair in FIG. 6A represents the normal flat panel scintillator (NaI & PMT) gamma cameras 24. To compare the FoM for various configurations, we will assert that both scintillator cameras in FIG. 6A are fitted with LEHR collimators (see TAB. 4). The efficiency, resolution, and cost of the following alternative designs B through J will be compared to this baseline reference configuration A. Thus the efficiency, resolution, and cost for design A, two NaI gamma cameras and two LEHR collimators, are each normalized to 1.0. Thus the relative Figure of Merit (FoM)=Efficiency/(Cost*Resolution$^2$)=1.0 to help compare the various design ideas. Table 4 below lists the comparisons.

The pair of flat panel gamma cameras in FIG. 6B represents flat panel CZT gamma cameras 22, as described in Table 2 and FIG. 2. We assert that the relative cost for a fully populated CZT gamma camera is about 2.75 times the cost of the baseline scintillator camera of the same field of view. We also assert that a CZT-LEGP collimator can be used with approximately 2.06 times greater efficiency than hexagonal LEHR, but the same average resolution. The FoM of this approach is 2.06/(2.75*1.00$^2$)=0.75.

FIGS. 6C and 6D depict two potential hybrid approaches to reduce the system cost of deploying CZT gamma cameras. The basic idea is to mix one scintillation camera with one CZT camera. In the pair of flat panel cameras of FIG. 6C "1 NaI+1 CZT" the scintillation camera is coupled to an LEGP collimator and the CZT camera has an LEHR-CZT collimator, resulting in 1.44 times the base efficiency, 1.03 times the resolution, and 1.88 times the cost, for a FoM of 0.73. Another alternative is in FIG. 6D wherein the flat panel scintillator camera has LEGP and the CZT camera has LEGP-CZT collimation. This results in relative efficiency of 1.82, relative resolution of 1.09, relative cost of 1.88, and FoM=0.81. These two hybrid options are for illustration and do not represent an optimized solution, which would require simulation and then confirmation using phantoms.

FIG. 6E introduces the concept of sparse acquisition by decimating the number of CZT aggregator modules deployed in the CZT gamma cameras. For purpose of illustration the decimation factor is two: half of the available locations for CZT modules are not filled. Those skilled in the art will recognize that other decimation factors and patterns may be usefully deployed. The pair of flat panel CZT gamma cameras in FIG. 6E "two Moving Slat CZT" gamma cameras shows 6 vertical slats 25 (4.4 cm wide×39.6 cm long) where nine AMs are located, alternating with 6 vertical spaces of white (also 4.4 cm wide) where there are no gamma detectors. Note that in this example embodiment, the upper and lower gamma cameras have a complementary pattern of occupied and vacant detector slats. Thus, in a standard SPECT acquisition where the two cameras are opposed by 180 degrees, all regions of the body are being imaged, so dynamic processes can be reliably sampled.

Figure 7:
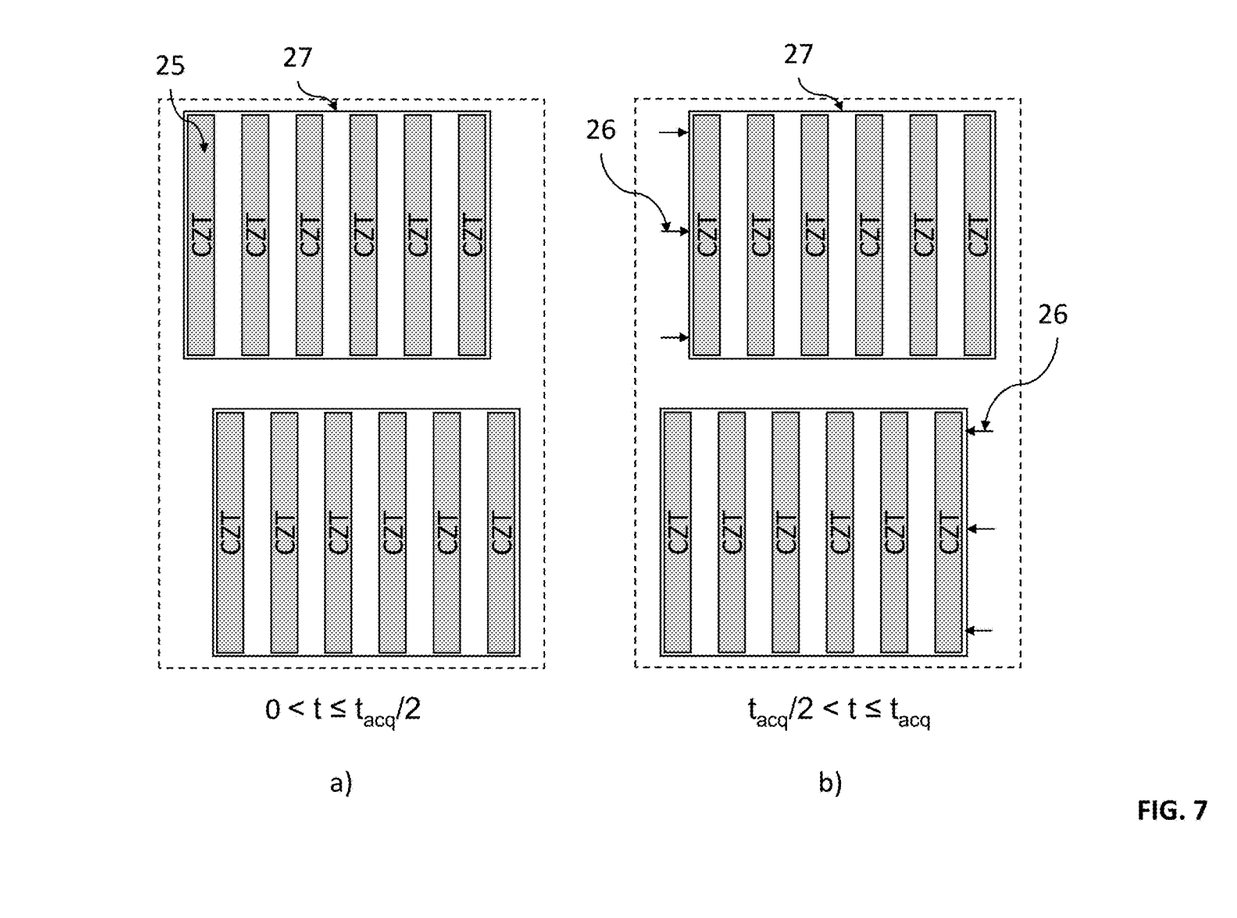
FIG. 7 depicts a pair of sparsely populated flat panel CZT gamma cameras in which detector motion is employed to compensate for the missing detectors.

As illustrated in FIG. 7, half of the acquisition time for a planar projection would be spent in the position shown in FIG. 7a, then all the slats would shift quickly right (arrows 26 depicted in the upper camera of FIG. 7b) or left (arrows 26 depicted in the lower camera of FIG. 7b) by 4.4 cm to the blank positions and the second half of the planar acquisition would be acquired. One skilled in the art will recognize various means for achieving this detector motion. By way of illustration, a mechanical frame 27 rigidly supports the sparsely populated gamma camera detector slats (columns) 25. The frame can be moved one column width (4.4 cm in this example) by one or more linear actuators 26. Of course, other components of a functioning gamma camera are not shown, such as electronic readout circuits, power, control circuits, radiation shielding, and collimator. The collimator can be fixed in position and cover the entire gamma camera area, or a slat of collimator can be attached to each slat of detectors and they can shift position together by means of linear actuators in a manner similar to that discussed for the detectors. Thus, 50% of the time is spent in each of two positions and a contiguous planar image is acquired. For this configuration embodiment in FIG. 6E, the relative efficiency and cost are both half of configuration 6B, thus the FoM=0.75 is the same.

In FIG. 6F with "1 NaI+1 Moving Slat CZT" gamma cameras, we combine the shifting motion slat concept of FIG. 6E with the hybrid concept shown in FIG. 6D, resulting in relative efficiency of 1.30 and cost of 1.19 with FoM=0.92. It will be apparent to one skilled in the art that the slats could be oriented in the horizontal direction with vertical shifting motion. It is also apparent that different decimation factors could be used to reduce cost. But efficiency and cost both depend linearly on the number of CZT detectors deployed.

FIG. 6G shows a variation on the concept of decimated slats (vertical or horizontal). In this variation there is no motion required to obtain projections of the gamma photon emission distribution of radiopharmaceuticals in the human body under examination. Instead, diverging fan (focal point behind detector) pixel-registered square-hole collimators are attached to each slat of gamma detectors. The field of view of adjacent fans will overlap in distal regions of the imaged body, but iterative maximum likelihood estimate reconstruction should have no difficulty in resolving redundant overlapping projections.

One perceived disadvantage may be that no planar projection is acquired as with parallel-hole collimators, but synthetic planar projections can be easily derived from the reconstructed 3D SPECT image. Without optimizing the possible diverging fan collimator designs, we estimate that for the embodiment in configuration 6G "two Slat CZT" gamma cameras and "two Fan" collimators, the relative efficiency is 1.5, but the relative resolution suffers from the diverging collimation, and the FoM is only about 0.36. Similarly, in a hybrid configuration embodiment 6H "1 NaI+1 Slat CZT" the FoM is only 0.56. As will be apparent to one skilled in the art, the concept of overlapping fan collimators is an inefficient compensation for decimation of CZT detectors intended to reduce cost.

Other embodiments for decimating the number of CZT AMs in a moving detector and collimator concept are contemplated, although they are not depicted here. For example, FIG. 6I illustrates a large checkerboard pattern for the factor of two decimation of CZT gamma detector AMs. Note that complementary detector patterns are shown for the upper and lower cameras, as also preferred for FIGS. 6E and 6G. As shown for illustration, each gray square consists of a 3×3 array of AMs forming a 13.2 cm×13.2 cm subarray 27. Other patterns, including different size checkerboard elements, will be apparent to one skilled in the art. As illustrated in FIGS. 6E and 6G, either motion of the slats 25 or use of diverging fan pixel-registered square-hole collimators could be deployed in this configuration. However, by way of illustration we prefer to deploy multiple-pinhole collimators positioned to illuminate each of the occupied detector subarrays 27. The use of multiple-pinhole collimation with overlapping projections has been proven in commercial products for small animal ("preclinical") SPECT (e.g., Trifoil Imaging of Chatsworth, Calif. and MiLabs B. V. of The Netherlands) and in human cardiac SPECT (i.e., GE Healthcare, a segment of General Electric Co.). Again, synthetic planar projections can be easily derived from the fully reconstructed SPECT image. Without optimizing the possible multi-pinhole collimator designs, we estimate that for embodiment 6I "two Checker CZT" a relative efficiency of about 2.0 (which could be higher), resolution of 0.87, and cost of 1.38 resulting in an FoM of 1.91. The hybrid variation for this configuration is in FIG. 6J "1 NaI+1 Checker CZT" with FoM of 1.44. These are the first two embodiments illustrated here that have FoM>1, indicating an improvement over the standard scintillator gamma cameras with LEHR collimators, as shown in FIG. 6A.

This preference for spatially separated smaller gamma cameras, such as the small 3×3 AM cameras 27 of FIG. 6I, can be generalized. This is one of the advantages of designing SPECT systems with modular CZT detectors. The use of multiple pinhole collimators can also be recommended. We have not discussed technical development risks and time-to-market considerations which may influence the choice of configuration, at least for the early introduction of CZT SPECT gamma cameras.

The use of curved detector panels, as indicated in FIG. 3b, would be available as a variation to all the previously discussed examples of preferred flat panel embodiments. We anticipate an improvement factor for relative efficiency of about 1.5 times. Thus, the FoM for a curved panel would be about 1.5 times that for configurations shown in FIG. 6B-J.

Ring CZT Gamma Cameras

Figure 8:
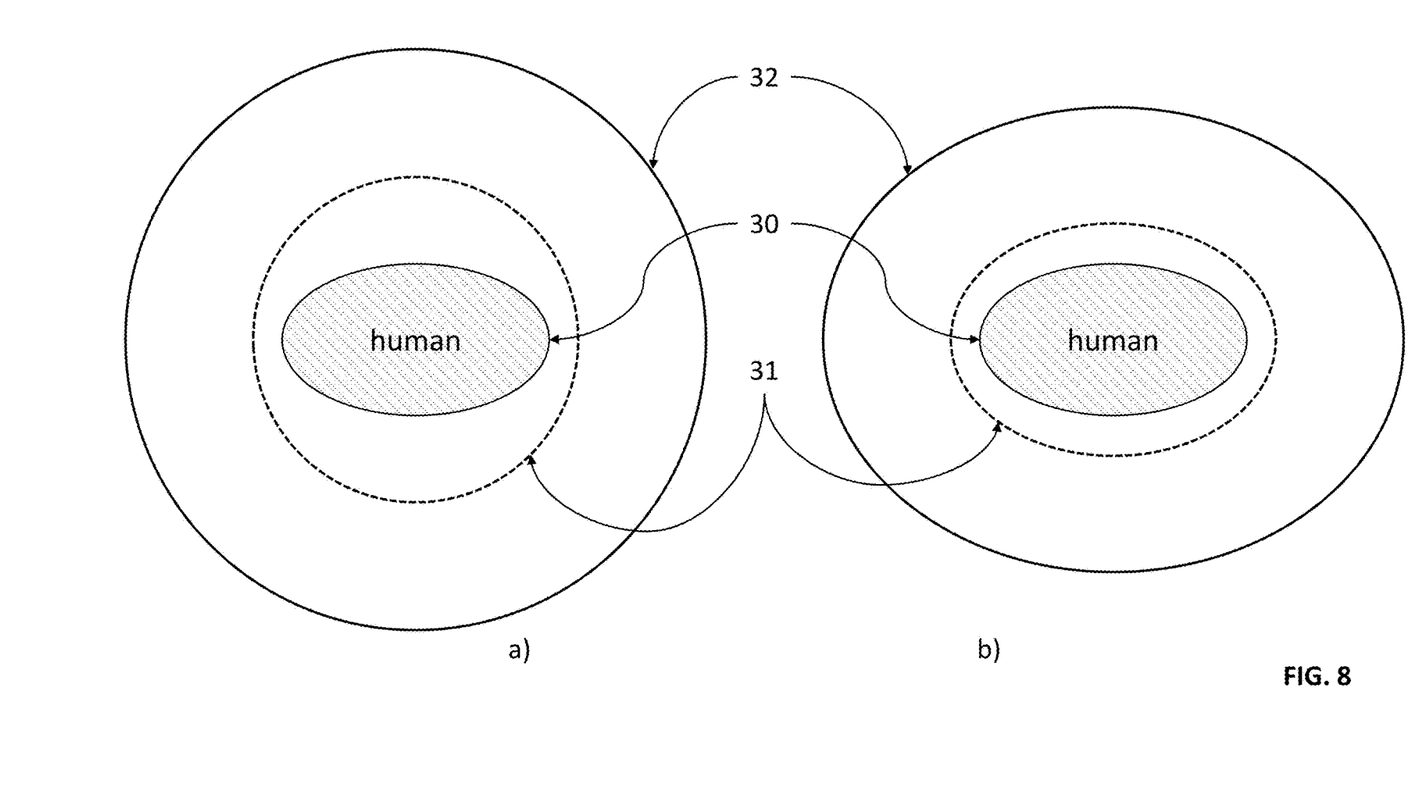
FIG. 8 depicts a circular or elliptical ring of CZT detectors surrounding a human body, similar to a PET scanning configuration.

FIG. 8 introduces another preferred embodiment of the present invention with a configuration variation that extends the concept of curved panels to the point where the two panels join to form a circular or elliptical ring of AMs 20 encircling the human body 30. In FIG. 8a a ring of detectors 32 about 1.2 m in diameter can be formed from 86 contiguous AMs 20 (86×4.4 cm=378.4 cm=π×120.4 cm=diameter). Recall that the cost of two fully populated flat-panel CZT gamma cameras was estimated to be 2.75 times the reference scintillation camera and that two×nine×12=216 AMs 20 were required. Thus the relative cost of a fully populated single ring of 86 AMs is 2.75×(86/216)=1.09. Of course, this invention contemplates that a tiled ring of CZT or other semiconductor gamma detector modules can be sparsely filled and the effects of missing detectors can be compensated by optimized collimation and potential detector motion.

Use of converging fan pixel-registered square-hole collimation would be technically feasible, but the spatial resolution would be poor since the distance from collimator to the interior human body is too large. A much better option is multiple pinhole collimation, for example located on a ring 31 of about 0.6 m diameter with about one pinhole per AM, for example. The density of pinholes could be varied and shutters could be employed to open or close various pinholes to manipulate the SPECT acquisition parameters. This arrangement would provide a magnification of about 1.0 at the central axis and increasing toward the surface of the human body. Based on experience with small animal multi-pinhole SPECT and human cardiac multi-pinhole SPECT, we estimate very conservatively that the relative efficiency of a single circular ring would be about 2.5 and thus an FoM of 3.0. Additional rings can be added, as with PET (Positron Emission Tomography) systems, and they are labeled configuration K, L, and M for one, two and 3 rings. Of course, cost and efficiency both scale linearly with the number of CZT AMs, so the FoM remains about 3.0 for all configurations, assuming fully populated rings. Again synthetic planar projections can be produced from the fully reconstructed 3D SPECT image.

Configurations N, O, and P represent one, two, and three elliptical rings as a variation on configurations K, L, and M with circular rings. Ellipses more closely follow the contours of most human bodies 30 (bariatric patients may have a more circular transaxial cross-section) and fewer CZT detectors are required for some cost savings. In the illustrative example shown in FIG. 8b, 79 AMs are deployed in each elliptical detector ring with principle axes of about 1.2 m and 1.0 m. The elliptical ring of multiple pinholes 31 would have proportional principle axes of 0.6 m and 0.5 m. We assume that the relative efficiency of an elliptical ring 32 would be similar to a circular ring 32, but the relative cost would be about 9% less, so the FoM would increase to about 3.27.

TAB. 4 lists the relative cost and efficiency (sensitivity) of the flat panel gamma camera configurations B-J depicted in FIG. 6 and the ring configurations K-P depicted in FIG. 8. It is apparent that much higher efficiencies can be achieved with ring CZT gamma cameras. This can be translated into a clinical tradeoff between better image quality and shorter examination times or lower patient doses. Apparently the better technical choice is a fully populated circular or elliptical ring of CZT gamma cameras, scalable to multiple rings (like PET). However, the best business choice may be a sparse flat or curved panel for a first generation CZT SPECT system, considering time to market and investment required to develop the first circular or elliptical CZT SPECT system.

Ring CZT Compton Gamma Cameras

FIG. 8 also illustrates another preferred embodiment of the present invention with another variation on the collimation. The technical risk is higher, so this configuration will likely not be the first introduced commercially, but the potential performance is game changing. The collimation in this preferred embodiment is provided by a Compton scatter ("electronic collimation") ring 31. Typically, lower atomic number elements have higher Compton scatter cross-sections, so 2D pixelated silicon (Si) gamma detectors are a good choice. To reconstruct a Compton scatter image requires information about the 3D position, energy, and timing of the atomic electron that undergoes a Compton scatter event in the Si detector as well as the 3D position, energy, and timing of the photoelectric interaction in the CZT. If the two events are close in time ("coincidence") and the energies add to the expected full peak energy of the emitted gamma photon, then the cone of response can be determined for the origin of the gamma photon. Typically, a stack of multiple Si 2D detectors (often pixelated using crossed-strip readout) can be used to enhance the Compton scatter probability. Without detailed modeling, we estimate, based upon general knowledge of one skilled in the art, that the efficiency of a Compton camera ring can be five to 20 times higher than the reference scintillator SPECT system. Also, because a ring of Si detector stacks must be added to the CZT ring, the relative cost is about two. Thus the FoM is about 2.5-10 times higher. We use the more conservative estimates in TAB. 4. Configurations Q, R, and S represent one, two, and 3 circular rings, while T, U, and V represent one, two, and three elliptical rings with FoM of 7.5 or 8.2 for circular or elliptical rings. It is apparent that much higher efficiencies can be achieved with Compton ring CZT gamma cameras. This can be translated into a clinical tradeoff between better image quality and shorter examination times or lower patient doses.

As a summary of the various configurations of CZT gamma cameras disclosed as embodiments of the present invention, the following TAB. 4 lists all the configurations and their approximate relative efficiencies, resolutions, costs, and Figures of Merit.

TABLE 4

Compilation of relative merits of the various embodiments for flat-panel, ring, and Compton ring SPECT systems using CZT gamma cameras. Note that efficiency and FoM for curved panel detectors of embodiments B through J may be a factor of 1.5 times higher.

| Label | Gamma Cameras | Collimators | Efficiency | Resolution | Cost | FoM |
|---|---|---|---|---|---|---|
| A | 2 NaI | 2 LEHR | 1.00 | 1.00 | 1.00 | 1.00 |
| B | 2 CZT | 2 LEGP-CZT | 2.06 | 1.00 | 2.75 | 0.75 |
| C | 1 NaI + 1 CZT | LEGP + LEHR-CZT | 1.44 | 1.03 | 1.88 | 0.73 |
| D | 1 NaI + 1 CZT | LEGP + LEGP-CZT | 1.82 | 1.09 | 1.88 | 0.81 |
| E | 2 Moving Slat CZT | 2 LEGP-CZT | 1.03 | 1.00 | 1.38 | 0.75 |
| F | 1 NaI + 1 Moving Slat CZT | LEGP + LEGP-CZT | 1.30 | 1.09 | 1.19 | 0.92 |
| G | 2 Slat CZT | 2 Fan | 1.50 | 1.75 | 1.38 | 0.36 |
| H | 1 NaI + 1 Slat CZT | LEHR + Fan | 1.25 | 1.37 | 1.19 | 0.56 |
| I | 2 Checker CZT | MPH | 2.00 | 0.87 | 1.38 | 1.91 |
| J | 1 NaI + 1 Checker CZT | LEHR + MPH | 1.50 | 0.94 | 1.19 | 1.44 |
| K | 1 Circular Ring | MPH | 2.50 | 0.87 | 1.09 | 3.00 |
| L | 2 Circular Rings | MPH | 5.01 | 0.87 | 2.19 | 3.00 |
| M | 3 Circular Rings | MPH | 7.51 | 0.87 | 3.28 | 3.00 |
| N | 1 Elliptical Ring | MPH | 2.50 | 0.87 | 1.01 | 3.27 |
| O | 2 Elliptical Rings | MPH | 5.01 | 0.87 | 2.01 | 3.27 |
| P | 3 Elliptical Rings | MPH | 7.51 | 0.87 | 3.02 | 3.27 |
| Q | 1 Circular Ring | Compton | 12.52 | 0.87 | 2.19 | 7.51 |
| R | 2 Circular Rings | Compton | 25.04 | 0.87 | 4.38 | 7.51 |
| S | 3 Circular Rings | Compton | 37.56 | 0.87 | 6.57 | 7.51 |
| T | 1 Elliptical Ring | Compton | 12.52 | 0.87 | 2.01 | 8.17 |
| U | 2 Elliptical Rings | Compton | 25.04 | 0.87 | 4.02 | 8.17 |
| V | 3 Elliptical Rings | Compton | 37.56 | 0.87 | 6.03 | 8.17 |

Higher Energy Isotope SPECT

The use of 5 mm thick CZT gives similar stopping power to 9.5 mm (3/8") NaI of about 85% for Tc-99m (140 keV), the most commonly used medical isotope for SPECT. This thickness is adequate for the most common medical isotopes, such as Tc-99m (140 keV), Tl-201 (70 keV), Xe-133 (81 keV), Ga-67 (90 keV), and I-123 (159 keV). Increasing the CZT thickness to 1.0 cm will increase the stopping power and thus the detection efficiency for higher energy medical isotopes, such as In-111 (171 & 245 keV) and I-131 (364 keV). Increasing the thickness of CZT to 1.0 cm results in higher efficiency for all isotopes and almost doubles the stopping power for 1-131 (364 keV). As will be apparent to one skilled in the art, the stopping power for non-normally incident gamma photons is increased by an interaction path longer by 1/cosine (incident angle). This enhanced efficiency favors somewhat the collimation techniques such as pinhole and fan.

With reference once again to FIG. 1 we disclose a method for reducing the cost of a CZT SPECT gamma camera designed to be efficient for both lower and higher energy SPECT isotopes. A D-Matrix™ aggregator module 20 with four gamma modules 21 could be built with two 0.5 cm thick CZT gamma modules 21 and two 1.0 cm thick gamma modules 21, preferably in a checkerboard pattern. In a preferred embodiment, the front (cathode) surface of the AM 20 would be flat, that is, the cathodes would be coplanar but the anodes would be staggered by the 0.5 cm difference in CZT sensor thickness. Iterative reconstruction of the SPECT projections would utilize a full physics description of the collimator-detector response, including the checkerboard CZT thickness pattern. As will be apparent to one skilled in the art, other patterns of mixing detector thicknesses can be devised to accomplish the same goal of providing for more efficient detection of higher energy isotopes, without increasing the price too dramatically.

While preferred embodiments of the present invention are shown and described, it is envisioned that those skilled in the art may devise various modifications of the present invention without departing from the spirit and scope of the appended claims.

We claim:

1. An imaging method, comprising:
receiving information regarding a gamma camera application, wherein the information identifies application requirements and performance requirements;
designing a gamma camera architecture for the gamma camera application, wherein the gamma camera comprises a collimator and at least one sparse tiled array of gamma detectors and wherein the gamma camera architecture comprises a collimator scheme and a pattern of the at least one tiled array of gamma detectors, wherein the collimator scheme compensates for a gamma camera motion and missing detectors in the at least one sparse tiled array;
the designing comprising:
selecting a collimator scheme for the collimator from a plurality of collimator schemes;
selecting a pattern of the at least one tiled array;
simulating an object of the gamma camera application, wherein the object comprises at least one gamma emission source;
modeling a response of the selected collimator scheme and selected pattern of the at least one tiled array to gamma emissions from the simulated object;
receiving a simulated data set for the model and identifying a performance figure of merit for the model from the simulated data set; and
identifying a gamma camera architecture for the gamma camera application by (i) iteratively performing the selecting a collimator scheme, selecting a pattern, simulating, modeling, and receiving by varying at least one of: collimator scheme and pattern, and (ii) selecting a gamma camera architecture for the gamma camera application based upon the performance figure of merit of the respective gamma camera architecture.

2. The imaging method of claim 1, wherein at least one of the performance requirements of an improvement of the performance figure of merit is selected from the group consisting of: a cost, an efficiency, and a resolution.

3. The imaging method of claim 1, wherein the at least one tiled array of gamma detectors comprises at least one of a flat panel, a curved panel, a circular ring, and an elliptical ring.

4. The imaging method of claim 1, wherein the collimator scheme comprises using at least one of a parallel hole collimator, a focused hole collimator, a slit-slat collimator, a rotating slat collimator, a multiple pinhole collimator, a coded aperture collimator, and a Compton scatter collimator.

5. The imaging method of claim 1, wherein the at least one tiled array of gamma detectors comprises tileable gamma photon detectors having an area less than 400 cm$^2$.

6. The imaging method of claim 1, wherein the at least one tiled array of gamma detectors comprises at least one of:
a scintillator with an optically-coupled photodetector and a semiconductor direct conversion detector.

7. The imaging method of claim 1, wherein the simulating an object comprises generating a simulated numerical distribution of a gamma emission radioactive material;
wherein the modeling comprises modeling an imaging system and a data acquisition sequence, the imaging system comprising a means to move the gamma camera; and
wherein the receiving a simulated data set comprises generating a simulated acquisition of imaging data using the simulated numeral distribution, the modeled imaging system, and the modeled data acquisition sequence and iteratively reconstructing the imaging data to obtain an imaged distribution.

8. The imaging method of claim 1, wherein the selecting a pattern comprises sparsely placing a gamma detector within the gamma camera and comprises using at least one scintillator gamma camera and at least one semiconductor gamma camera.

9. The imaging method of claim 1, wherein the selecting a pattern comprises removing at least one gamma detector from the at least one tiled array.

10. The imaging method of claim 1, wherein the selecting a pattern comprises removing at least one column or row of gamma detectors from the at least one tiled array.

11. The imaging method of claim 1, wherein the selecting a pattern comprises removing gamma detectors in a checkerboard pattern from the at least one tiled array.

12. The imaging method of claim 1, wherein the collimator has design parameters and wherein the selecting a collimator scheme comprises adjusting the collimator design parameters to affect at least one of efficiency and spatial resolution.

13. The imaging method of claim 1, further comprising a step of acquiring imaging data during a period of time, and wherein the identifying a gamma camera architecture comprises at least one of moving the gamma detector from a first detector position to a second detector position and moving the collimator from a first collimator position to a second collimator position during a period of acquiring imaging data.

14. The imaging method of claim 1, wherein the performance figure of merit comprises an efficiency divided by a product of spatial resolution squared and a gamma camera cost.

15. A gamma camera, comprising:
a collimator;
at least one tiled array of gamma detectors;
a memory device that stores instructions executable by the processor to:

receive information regarding a gamma camera application, wherein the information identifies application requirements and performance requirements;

design a gamma camera architecture for the gamma camera application, wherein the gamma camera architecture comprises at least one collimator scheme and a pattern of the at least one sparse tiled array of gamma detectors, wherein the at least one collimator scheme is selected from a plurality of collimator schemes, wherein the collimator scheme compensates for a gamma camera motion and missing detectors in the at least one sparse tiled array;

the designing comprising:

selecting a pattern of the at least one tiled array;

simulating an object of the gamma camera application, wherein the object comprises at least one gamma emission source;

modeling a response of the selected collimator scheme and selected pattern of the at least one tiled array to gamma emissions from the simulated object;

receiving a simulated data set for the model and identifying a performance figure of merit for the model from the simulated data set; and identifying a gamma camera architecture for the gamma camera application by (i) iteratively performing the selecting a collimator scheme, selecting a pattern, simulating, modeling, and receiving by varying at least one of: collimator scheme and pattern, and (ii) selecting a gamma camera architecture for the gamma camera application based upon the performance figure of merit of the respective gamma camera architecture.

16. The gamma camera of claim 15, wherein at least one of the performance requirements defines an improvement of the performance figure of merit over a previous gamma camera architecture.

17. The gamma camera of claim 15, wherein the at least one tiled array of gamma detectors comprises at least one of a flat panel, a curved panel, a circular ring, and an elliptical ring.

18. The gamma camera of claim 15, wherein the collimator scheme comprises using at least one of a parallel hole collimator, a focused hole collimator, a slit-slat collimator, a rotating slat collimator, a multiple pinhole collimator, a coded aperture collimator, and a Compton scatter collimator.

19. The gamma camera of claim 15, wherein the at least one tiled array of gamma detectors comprises tileable gamma photon detectors having an area less than 400 cm$^2$.

20. The gamma camera of claim 15, wherein the at least one tiled array of gamma detectors comprises at least one of:

a scintillator with an optically-coupled photodetector and a semiconductor direct conversion detector.

21. The gamma camera of claim 15, wherein the simulating an object comprises generating a simulated numerical distribution of a gamma emission radioactive material;

wherein the modeling comprises modeling an imaging system and a data acquisition sequence, the imaging system comprising a means to move the gamma camera; and wherein the receiving a simulated data set comprises generating a simulated acquisition of imaging data using the simulated numeral distribution, the modeled imaging system, and the modeled data acquisition sequence and iteratively reconstructing the imaging data to obtain an imaged distribution.

22. The gamma camera of claim 15, wherein the selecting a pattern comprises sparsely placing a gamma detector within the gamma camera and comprises using at least one scintillator gamma camera and at least one semiconductor gamma camera.

23. The gamma camera of claim 15, wherein the selecting a pattern comprises removing at least one gamma from the at least one tiled array.

24. The gamma camera of claim 15, wherein the selecting a pattern comprises removing at least one column or row of gamma detectors from the at least one tiled array.

25. The gamma camera of claim 15, wherein the selecting a pattern comprises removing gamma detectors in a checkerboard pattern from the at least one tiled array.

26. The gamma camera of claim 15, wherein the collimator has design parameters and wherein the selecting a collimator scheme comprises adjusting the collimator design parameters to affect at least one of efficiency and spatial resolution.

27. The gamma camera of claim 15, the camera capable of acquiring imaging data during a period of time, and wherein the identifying a gamma camera architecture comprises at least one of moving the gamma detector from a first detector position to a second detector position and moving the collimator from a first collimator position to a second collimator position during a period of acquiring imaging data.

28. The gamma camera of claim 15, wherein the performance figure of merit comprises an efficiency divided by a product of spatial resolution squared and a gamma camera cost.

* * * * *